United States Patent
Clark et al.

(10) Patent No.: US 10,234,269 B2
(45) Date of Patent: Mar. 19, 2019

(54) FIBER OPTIC SHAPE SENSING TECHNOLOGY FOR ENCODING OF NDE EXAMS

(71) Applicant: GE-Hitachi Nuclear Energy Americas LLC, Wilmington, NC (US)

(72) Inventors: Timothy W. Clark, Wilmington, NC (US); Robert William Viren, Wilmington, NC (US)

(73) Assignee: GE-Hitachi Nuclear Energy Americas LLC, Wilmington, NC (US)

( * ) Notice: Subject to any disclaimer, the term of this patent is extended or adjusted under 35 U.S.C. 154(b) by 616 days.

(21) Appl. No.: 14/736,473

(22) Filed: Jun. 11, 2015

(65) Prior Publication Data
US 2016/0363436 A1 Dec. 15, 2016

(51) Int. Cl.
 *G01B 11/00* (2006.01)
 *G01L 1/24* (2006.01)
 (Continued)

(52) U.S. Cl.
 CPC ............ *G01B 11/002* (2013.01); *G01L 1/246* (2013.01); *G01N 29/043* (2013.01); *G01N 29/14* (2013.01);
 (Continued)

(58) Field of Classification Search
 CPC ..... A61B 8/4254; G01B 11/002; G01L 1/246; G01N 2291/0289; G01N 27/902; G01N 29/043; G01N 29/14; G01N 29/265
 (Continued)

(56) References Cited

U.S. PATENT DOCUMENTS

| 6,122,967 A | 9/2000 | Sword |
| 7,743,660 B2 | 6/2010 | Marsh et al. |

(Continued)

FOREIGN PATENT DOCUMENTS

WO    WO-9401766 A1    1/1994

OTHER PUBLICATIONS

"Fiber Optic Shape Sensing", Luna Innovations Incorporated, Jun. 21, 2013, document #: SS00021-D-TS, revision 003, 6 pages.
(Continued)

*Primary Examiner* — John H Le
(74) *Attorney, Agent, or Firm* — Harness, Dickey & Pierce, P.L.C.

(57) ABSTRACT

A system and method for conducting Non-Destructive Examination (NDE) inspections and integrating inspection data with encoding information may include a NDE probe configured to conduct a non-destructive examination of an object, a shape sensing fiber optic cable attached to the NDE probe, the fiber optic cable configured to receive a frequency of light and to reflect the received light, a fiber optic cable shape sensing detector configured to generate light of the frequency, measure the shape of the shape sensing fiber optic cable based on the reflected light from the shape sensing fiber optic cable, and determine position information and orientation information of the NDE probe based on the measured shape of the fiber optic cable, and a processor configured to encode the examination data, the encoding including correlating the position information and the orientation information with the examination data.

28 Claims, 6 Drawing Sheets

(51) Int. Cl.
*G01N 29/04* (2006.01)
*G01N 29/265* (2006.01)
*G01N 29/14* (2006.01)
*A61B 8/00* (2006.01)
*G01N 27/90* (2006.01)

(52) U.S. Cl.
CPC .......... *G01N 29/265* (2013.01); *A61B 8/4254* (2013.01); *G01N 27/902* (2013.01); *G01N 2291/0289* (2013.01)

(58) Field of Classification Search
USPC ...... 702/153; 250/215, 227.14; 356/43, 511, 356/601; 385/12, 13
See application file for complete search history.

(56) References Cited

U.S. PATENT DOCUMENTS

| 7,772,541 | B2* | 8/2010 | Froggatt | .............. G01M 11/083 250/226 |
| 7,781,724 | B2 | 8/2010 | Childers et al. | |
| 9,625,254 | B2* | 4/2017 | Manzke | .................. G01B 11/24 |
| 2013/0131499 | A1 | 5/2013 | Chan et al. | |
| 2013/0150732 | A1 | 6/2013 | Manzke et al. | |
| 2013/0272093 | A1 | 10/2013 | Chen et al. | |
| 2014/0183341 | A1 | 7/2014 | Glass, III et al. | |
| 2014/0184750 | A1 | 7/2014 | Thigpen et al. | |
| 2014/0240713 | A1 | 8/2014 | Kemp | |
| 2015/0124264 | A1* | 5/2015 | Ramachandran | ...... G01B 11/24 356/601 |

OTHER PUBLICATIONS

International Search Report and Opinion issued in connection with corresponding EP Application No. 16173822.4 dated Nov. 11, 2016.
Lane, "The Inspection of Curved Components Using Flexible Ultrasonic Arrays and Shape Sensing Fibres", Case Studies in Nondestructive Testing and Evaluation, Apr. 2014, pp. 13-18, vol. No. 1, Issue No. 1.

* cited by examiner

FIBER OPTIC SHAPE SENSING TECHNOLOGY FOR ENCODING OF NDE EXAMS

BACKGROUND

Non-destructive examinations (NDE) is a group of analysis techniques used to inspect or otherwise examine one or more properties of a material, substance, component, and/or system without causing damage to the material, substance, component, and/or system being evaluated, inspected, and/or examined. The terms nondestructive testing (NDT), nondestructive inspection (NDI), and nondestructive evaluation (NDEv) are also commonly used to describe NDE. Because NDE does not permanently alter the article being examined, NDE may be a valuable technique for product evaluation, troubleshooting, and/or research.

Common NDE methods include acoustic emission testing (AE), electromagnetic testing (ET), laser testing methods (LM), leak testing (LT), magnetic flux leakage (MFL), liquid penetrant testing (PT), magnetic particle testing (MT), neutron radiographic testing (NR), radiographic testing (RT), thermal/infrared testing (IR), ultrasonic testing (UT), vibration analysis (VA), visual testing (VT), remote visual inspection (RVI), eddy-current testing (ECT), and/or low coherence interferometry (LCI). NDE is commonly used in nuclear engineering, forensic engineering, mechanical engineering, electrical engineering, civil engineering, systems engineering, aeronautical engineering, nautical engineering, astronautical engineering, medicine, veterinary medicine, scientific research, and the like.

Materials, components, and/or systems used in industrial settings, such as nuclear power plants (NPPs), are typically required to undergo NDE or other like inspections. NDEs are typically performed by placing an NDE probe on an object to be examined. The probe then transmits an electric current, induces a magnetic field, or transmits ultrasonic waves, and the like into the examination object. A detection system is then used to analyze the electromagnetic radiation, sound waves, or induced magnetic field in view of the inherent properties of the materials and geometry of the examined object. Based on the analysis, examination data is produced. The examination data may be analyzed and/or processed to determine one or more characteristics of the examined object. The characteristics may indicate weld characteristics, a thickness of the object, structural mechanics, and the like. The examination data is then correlated with a position and orientation of the probe. The process of correlating the examination data with the position and/or orientation of the probe may be referred to as "encoding" the examination data. The aforementioned process is then performed multiple times by changing the position and orientation of the probe and probe type. An indication of a deficiency (e.g., a crack, a fracture, and the like), including a position and orientation and approximate size of the deficiency (e.g., whether the crack or fracture is perpendicular or parallel to a weld), may be determined once a sufficient amount of examination data has been encoded.

An NDE and analysis may be performed manually (i.e., "manual examination") or automatically (i.e., "automatic examination"). Manual examination typically requires a human operator to position and orient the probe on the examination object at a particular position of the examination object, analyzing the data produced, and then repositioning the probe onto the next examination position of the examination object. When a possible indication is observed, i.e., a potential issue in or on the examination object that requires further inspection, such as a potential crack or leak in a pipe, the operator will make physical marks in the inspection area to approximate size and orientation of the indication. These data will then be transcribed typically to paper, or in some cases single data points will be saved, but they may not be encoded. However, successful and consistent application of manual examination depends heavily on operator training, experience, and diligence because the operator is required to cover the entire inspection area of the examination object with the examination probe without missing a point or area of the examination object. Additionally, operators involved in manual examination and analysis must undertake numerous training and/or certification courses in order to conduct a proper manual examination. Furthermore, because manual examination requires a human operator to properly place a probe on an object and properly change the position and orientation of the probe, human error in handling the probe, such as not properly positioning the probe on the examination object (e.g., the probe is not situated flush and at a 90 degree position on the examination object), may adversely affect the quality and accuracy of the encoded examination data. Manual examinations also do not provide a real-time history of the areas of the pipe that have been examined by the examination probe.

Automatic examinations are examinations that are performed by one or more electro-mechanical machines. During automatic examination, an electro-mechanical machine may be incorporated into an inspection system and/or probe, and the electro-mechanical machine may perform similar positioning and orienting functions as a human operator would during a manual examination. Such electro-mechanical machines typically include a positioning and/or orientation detection device, such as an encoder wheel, which allows an operator to determine a position and/or orientation of the probe However, these electro-mechanical machines may require complex arrangements of machinery, tracks, and/or propulsion systems in order to change a position and/or orientation of the probe. For example, a probe incorporating an electro-mechanical machine may require a specialized track to be built on an examination object. By way of another example, propulsion device, such as a water thruster, may be required where the object is in an underwater environment. Building complex arrangements of machinery, tracks, and/or propulsion systems may require extensive planning and may be time consuming and expensive. Additionally, each electro-mechanical machine must be custom built for the examination object that it is designed to inspect, thereby increasing the cost of examining large complexes, such as nuclear reactors, that require the NDE examination of multiple objects. Also, there may be situations where a conventional automated examination electro-mechanical device physically is incapable of performing an examination of an object, for example, if there is an examination object that is situated in areas that do not provide enough clearance for electro-mechanical machines to operate and/or examine an examination object, or, if the examination object is of a shape that is not conducive to being examined by an electro-mechanical machine. Additionally, while automated examination electro-mechanical machines may position a examination probe at the proper angle for examining an object (e.g., 90 degrees), there are instances where it is preferable to also examine the object using an examination probe at a non-ideal angle, because the examination data from the non-ideal angle may produce indications that may not have been observable when the examination probe is held at the proper angle.

SUMMARY

At least one example embodiment relates to a system for conducting Non-Destructive Examination (NDE) inspections and/or integrating inspection data with encoding information.

In at least one example embodiment a system for conducting Non-Destructive Examination (NDE) inspections and integrating inspection data with encoding information may include a NDE probe configured to conduct a non-destructive examination of an object, a shape sensing fiber optic cable attached to the NDE probe, the fiber optic cable configured to receive a frequency of light and to reflect the received light, a fiber optic cable shape sensing detector configured to generate light of the frequency, measure the shape of the shape sensing fiber optic cable based on the reflected light from the shape sensing fiber optic cable, and determine position information and orientation information of the NDE probe based on the measured shape of the fiber optic cable, and a processor configured to encode the examination data, the encoding including correlating the position information and the orientation information with the examination data, and the encoded examination data may be used to determine whether there is an indication within the object.

Some example embodiments provide that the fiber optic cable may be configured to receive varying frequencies of light and the fiber optic cable shape sensing detector may be configured to generate the varying frequencies of light.

Some example embodiments provide that the shape sensing fiber optic cable may include at least one fiber optic core.

Some example embodiments provide that the shape sensing fiber optic cable may include a plurality of fiber optic cores woven together in a helical manner.

Some example embodiments provide that the shape sensing fiber optic cable may include a plurality of fiber optic cores configured in a geometric shape.

Some example embodiments provide that the NDE probe may include an ultrasonic transducer/receiver.

Some example embodiments provide that the determined position information may include information regarding the X-axis position, Y-axis position, and Z-axis position of the NDE probe, and that the determined orientation information may include information regarding the yaw angle, pitch angle, and roll angle of the NDE probe.

Some example embodiments provide that the processor may be configured to encode the examination data in real-time.

Some example embodiments provide that the NDE probe may be coupled to a robot configured to traverse the object.

Some example embodiments provide that the processor may be configured to produce a 3D representation of the object based on the encoded information and transmit the 3D representation of the object to a display.

Some example embodiments provide that the shape sensing fiber optic cable may include Bragg gratings.

Some example embodiments provide that the fiber optic cable shape sensing detector may be configured to measure the shape of the shape sensing fiber optic cable by comparing the frequency of the reflected light with the frequency of the generated light.

Some example embodiments provide that the fiber optic cable shape sensing detector may be configured to measure the shape of the shape sensing fiber optic cable by comparing a Rayleigh back scatter pattern of the shape sensing fiber optic cable with a reference Rayleigh back scatter pattern.

Some example embodiments provide that the NDE probe may perform at least one of an acoustic emission testing (AE), an electromagnetic testing (ET), a laser testing methods (LM), a leak testing (LT), a magnetic flux leakage (MFL), a liquid penetrant testing (PT), a magnetic particle testing (MT), a neutron radiographic testing (NR), a radiographic testing (RT), a thermal/infrared testing (IR), an ultrasonic testing (UT), a vibration analysis (VA), a visual testing (VT), a remote visual inspection (RVI), an eddy-current testing (ECT), and a low coherence interferometry (LCI).

At least one example embodiment relates to a method for conducting Non-Destructive Examination (NDE) inspections and integrating inspection data with encoding information.

In at least one example embodiment a method for conducting Non-Destructive Examination (NDE) inspections and integrating inspection data with encoding information is provided. The method may include conducting a non-destructive examination of an object using a NDE probe, determining a shape of a shape sensing fiber optic cable attached to the NDE probe, the determining including, generating, by a fiber optic cable shape sensing detector, a frequency of light, reflecting, by the shape sensing fiber optic cable, the frequency of light, measuring, by the fiber optic cable shape sensing detector, the shape of the shape sensing fiber optic cable based on the reflected light from the shape sensing fiber optic cable, and determining position information and orientation information of the NDE probe based on the measured shape of the fiber optic cable, encoding the examination data, the encoding including correlating the position information and the orientation information with the examination data, and determining whether there may be an indication in the object based on the encoded examination data.

Some example embodiments provide that the generating the frequency of light may include generating varying frequencies of light and the reflecting the frequency of light may include reflecting the varying frequencies of light.

Some example embodiments provide that the determining the shape of the shape sensing fiber optic cable may include determining a shape of at least one fiber optic core.

Some example embodiments provide that the determining the shape of the shape sensing fiber optic cable may include determining shapes of a plurality of fiber optic cores woven together in a helical manner.

Some example embodiments provide that the determining the shape of the shape sensing fiber optic cable may include determining shapes of a plurality of fiber optic cores configured in a geometric shape.

Some example embodiments provide that the conducting the non-destructive examination of the object may include conducting an ultrasonic examination of the object.

Some example embodiments provide that the determining position information may include determining the X-axis position, Y-axis position, and Z-axis position of the NDE probe, and the determining orientation information may include determining the yaw angle, pitch angle, and roll angle of the NDE probe.

Some example embodiments provide that the encoding may be conducted in real-time.

Some example embodiments provide that the conducting may be performed by a robot coupled to the NDE probe, the robot configured to traverse the object.

Some example embodiments provide that the method may further include producing a 3D representation of the object based on the encoded information, and transmitting the 3D representation of the object to a display.

Some example embodiments provide that the measuring the shape of the shape sensing fiber optic cable may include comparing the frequency of the reflected light with the frequency of the generated light.

Some example embodiments provide that the measuring the shape of the shape sensing fiber optic cable may include measuring the frequency of light reflected off of at least one Bragg grating within the shape sensing fiber optic cable.

Some example embodiments provide that the measuring the shape of the shape sensing fiber optic cable may include measuring a Rayleigh back scatter pattern of the shape sensing fiber optic cable and comparing the measured Rayleigh back scatter pattern with a reference Rayleigh back scatter pattern of the shape sensing fiber optic cable.

Some example embodiments provide that the conducting may include performing at least one of: an emission testing (AE), an electromagnetic testing (ET), a laser testing methods (LM), a leak testing (LT), a magnetic flux leakage (MFL), a liquid penetrant testing (PT), a magnetic particle testing (MT), a neutron radiographic testing (NR), a radiographic testing (RT), a thermal/infrared testing (IR), an ultrasonic testing (UT), a vibration analysis (VA), a visual testing (VT), a remote visual inspection (RVI), an eddy-current testing (ECT), and a low coherence interferometry (LCI).

BRIEF DESCRIPTION OF THE DRAWINGS

The accompanying drawings, which are incorporated in and constitute a part of the specification, illustrate one or more example embodiments and, together with the description, explain these example embodiments. In the drawings.

DETAILED DESCRIPTION

Figure 1:
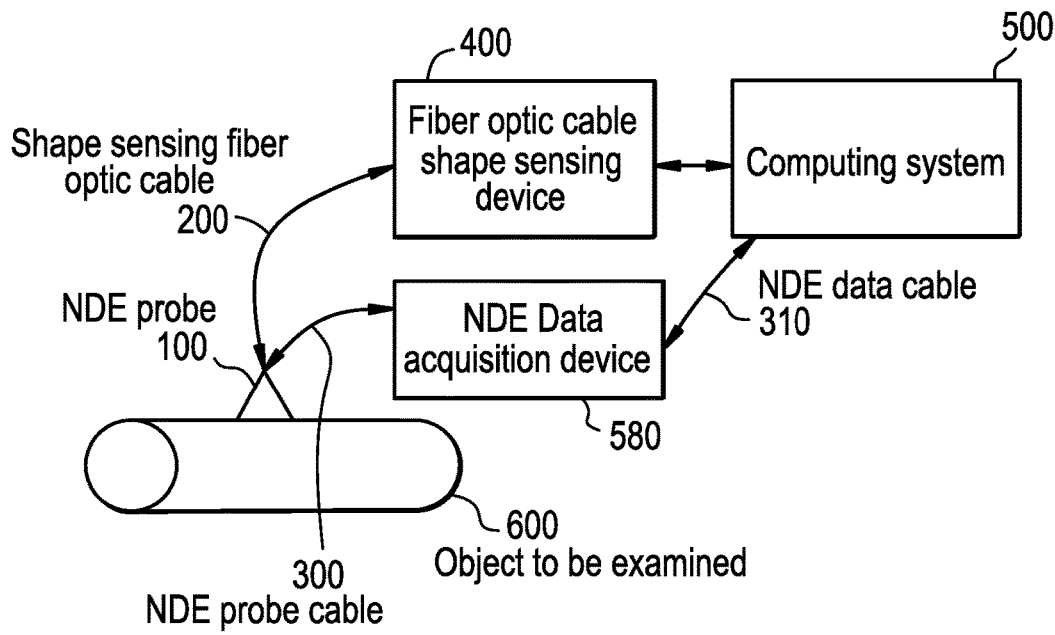
FIG. 1 illustrates a system for encoding examination data of an object, according to an example embodiment.

Various example embodiments will now be described more fully with reference to the accompanying drawings in which some example embodiments are shown.

Detailed example embodiments are disclosed herein. However, specific structural and functional details disclosed herein are merely representative for purposes of describing the example embodiments. The embodiments may, however, may be embodied in many alternate forms and should not be construed as limited to only the example embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Specific details are provided in the following description to provide a thorough understanding of the example embodiments. However, it will be understood by one of ordinary skill in the art that example embodiments may be practiced without these specific details. For example, systems may be shown in block diagrams in order not to obscure the example embodiments in unnecessary detail. In other instances, well-known processes, structures and techniques may be shown without unnecessary detail in order to avoid obscuring example embodiments.

Also, it is noted that example embodiments may be described as a process depicted as a flowchart, a flow diagram, a data flow diagram, a structure diagram, or a block diagram. Although a flowchart may describe the operations as a sequential process, many of the operations may be performed in parallel, concurrently or simultaneously. In addition, the order of the operations may be re-arranged. A process may be terminated when its operations are completed, but may also have additional steps not included in the figure. A process may correspond to a method, a function, a procedure, a subroutine, a subprogram, etc. When a process corresponds to a function, its termination may correspond to a return of the function to the calling function or the main function.

Moreover, as disclosed herein, the term "memory" may represent one or more devices for storing data, including random access memory (RAM), magnetic RAM, core memory, and/or other machine readable mediums for storing information. The term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" may include, but is not limited to, portable or fixed storage devices, optical storage devices, wireless channels, and various other mediums capable of storing, containing or carrying instruction(s) and/or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a storage medium. A processor(s) may perform the necessary tasks.

A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Example embodiments are discussed herein as being implemented in a suitable computing environment. Although not required, example embodiments will be described in the general context of computer-executable instructions, such as program modules or functional processes, being executed by one or more computer processors or CPUs. Generally, program modules or functional processes include routines, programs, objects, components, data structures, etc. that performs particular tasks or implement particular data types. The program modules and functional processes discussed herein may be implemented using existing hardware in existing communication networks. For example, program modules and functional processes discussed herein may be implemented using existing hardware at existing network elements or control nodes. Such existing hardware may include one or more digital signal processors (DSPs), application-specific-integrated-circuits, field programmable gate arrays (FPGAs) computers or the like.

At least one of the example embodiments of encoding examination data of an object allow for examination encoding to occur with little or no complex arrangements of machinery, tracks, and/or resolvers to determine a NDE probe position. The application of shape sensing fiber optic cables and a computing system allows for the encoding of examinations with less reliance on costly setups, customized tracks, and/or customized hardware. At least one of the example embodiments also allow for examinations to be performed on objects having complex geometry and/or objects covering large areas.

At least one of the example embodiments integrates NDE probe data with position information and/or orientation information streamed from the sensor. The NDE probe data may be procured by way of ultrasonic testing, an eddy current testing, phased array testing, and the like. The synchronization and capture of this data produces a data stream similar to traditional methods of examination data encoding without the physical constraints of bulky hardware and/or other the other traditional examination setups.

As used herein, the term "position" may refer to a location or point that one object may be in relation to another object. For example, position information may indicate a point that an NDE probe is located on an examination object in a two-dimensional (2D) or three-dimensional (3D) space. As used herein, the term "orientation" may refer to a placement of an object, such as an NDE probe, in relation to another object. For example, orientation information may indicate an angle at which an NDE probe is placed in relation to an object that is undergoing an examination. Together, the position information and the orientation information may indicate how an object is placed in a defined 2D or 3D space. Furthermore, the term "encode", "encoding", and the like, as used herein, may refer to a process of correlating examination data with position information and/or orientation information, or otherwise defining a relationship between examination data and position information and/or orientation information.

It should be noted that, although the example embodiments may be described in connection with nuclear safety related systems, the example embodiments may also apply to any industry where the examination one or more materials, components, and/or other like objects are desired. Such industries may include nuclear engineering, forensic engineering, mechanical engineering, electrical engineering, civil engineering, systems engineering, aeronautical engineering, nautical engineering, astronautical engineering, medicine, veterinary medicine, scientific research and/or any other like disciplines that deal with design, construction, examination, and/or maintenance of objects where non-destructive examinations are desired and/or required, such as physical structures and objects.

Some example embodiments include at least one shape sensing fiber optic cable ("SSFOC") that may be affixed or otherwise attached to an NDE probe via a housing, and a fiber optic cable shape sensing device ("shape sensing device"), such that the shape sensing device may determine the shape of the SSFOC, which may then be used to determine the position of the NDE probe. The NDE probe housing may include a fixture and/or attachment surface that may be used to attach the NDE probe to an object for performing an examination on the object. The fixture may be customized to fit the object based on at least one criterion of the object. Such a criterion of the object may include a geometry and/or shape of the object, a material and/or composition of the object, a position of the object in relation to one or more other objects, a location and/or environment in which the object is located, and/or other like criteria.

Some example embodiments include an NDE probe that is capable of transmitting, or configured to transmit, examination data in real-time to a computing system with minimal latency. The examination data may be encoded, correlated, or otherwise matched with position and/or orientation data that is detected by the sensor. A high latency in transmitting the examination data to the computing system may delay or otherwise hinder synchronization between the examination data derived from the NDE probe with the position information and/or orientation information derived from the SSFOC and shape sensing device, and may reduce the computing system's ability to properly encode, correlate, or otherwise match the examination data with the position information and/or orientation information. The examination data may also be encoded after the NDE inspection by the operator has been completed.

Some example embodiments include a computing system capable of handling and receiving data streams of the examination data, which are received from the NDE probe. The computing system may include at least one processor, a computer-readable medium, and/or a receiver (or optionally, a transmitter/receiver combination device, and/or a transceiver). The computing system may also include one or more hardware modules, software modules, or any combination thereof, which may allow the processor of the computing system to determine a position and/or orientation of the NDE probe based on information received from the shape sensing device. The information received from the shape sensing device may indicate a position and/or orientation of the NDE probe. The computing system may also include one or more hardware modules, software modules, or any combination thereof, which may allow the processor of the computing system to encode, correlate, or otherwise determine a statistical relationship between the determined position and/or orientation of the NDE probe with the examination data received from the NDE probe. The position information may include information regarding the position of the NDE probe in two- or three-dimensions, including the X-axis, Y-axis, and/or Z-axis. The orientation information may include information regarding the angular orientation of the NDE probe in two- or three-angles of rotation, including the pitch, roll, and/or yaw angles. Additionally, the position information and the orientation information may further include time information that may indicate the point in time that the position information and/or orientation information was measured, determined, calculated, captured and/or sensed.

Some example embodiments may include a fiber optic cable reference tool that may be used to define a reference point for the shape sensing fiber optic cable that may be used, at least in part, to determine the position information and orientation information of the SSFOC. The reference tool may be configured to remain in a substantially static position for a duration of the NDE inspection process. Example embodiments also allow for the computing system or the shape sensing device to determine the reference point without the use of a separate fiber optic cable reference tool.

FIG. 1 illustrates a shape sensing fiber optic cable NDE examination data encoding system, according to an example embodiment. The shape sensing fiber optic cable NDE examination data encoding system may include NDE probe 100, shape sensing fiber optic cable 200, NDE probe cable 300 and NDE data cable 310, fiber optic cable shape sensing device 400, NDE data acquisition device 580, computing system 500, and examination object 600.

According to various example embodiments, NDE probe 100 may be any device that may be configured to sense, detect, capture, measure or otherwise obtains NDE examination information of an object (e.g., object 600). The NDE probe may include one or more hardware devices and/or software components configured to transmit one or more signals, such as ultrasonic pulse-waves, one or more types of electromagnetic radiation waves, a magnetic field, eddy-currents, and/or the like (e.g., signals) into an object (e.g., object 600). The NDE probe may be configured to detect, measure, and/or analyze an energy level of the signals penetrating the examination object in order to determine one or more characteristics of the examination object. The determined characteristics may indicate an internal structure, flaw and/or deficiency, a thickness of the object, image of the object, and the like.

In various example embodiments, the NDE probe 100 may include a transducer or any other like device that is configured to convert a signal in one form of energy to another form of energy (not shown). Energy types include (but are not limited to) electrical, electromagnetic (including light), chemical, acoustic, thermal energy, and the like. Such a transducer may include the use of a sensor/detector, where the sensor/detector is configured to detect a parameter in one form and report it in another form of energy. In such embodiments, the reporting form of energy may include an analog signal, a digital data stream, and the like. Example embodiments of the NDE probe will be discussed in further detail in connection with FIG. 2.

In various example embodiments, the NDE probe 100 may include a physical computer hardware device capable of communicating with one or more other hardware computing devices (e.g., NDE data acquisition device 580, computing system 500, and the like) via a communications interface. The NDE probe 100 may also include a network interface configured to connect NDE probe 100 to one or more other hardware computing devices (e.g., NDE data acquisition device 580, computing system 500 and the like) wirelessly via a transmitter and a receiver (or optionally a transceiver) and/or via a wired connection (e.g., NDE probe cable 300 and NDE data cable 310) using a communications port. NDE probe may be configured to send/receive data to/from one or more other hardware computing devices, and/or network devices, such as a router, switch, or other like network devices, via the network interface using the wired connection and/or the wireless connection. The wireless transmitter/receiver and/or transceiver may be configured to operate in accordance with the IEEE 802.11-2007 standard (802.11), the Bluetooth standard, and/or any other like wireless standards. The communications port may be configured to operate in accordance with a wired communications protocol, such as a serial communications protocol (e.g., the Universal Serial Bus (USB), FireWire, Serial Digital Interface (SDI), and/or other like serial communications protocols), a parallel communications protocol (e.g., IEEE 1284, Computer Automated Measurement And Control (CAMAC), and/or other like parallel communications protocols), and/or a network communications protocol (e.g., Ethernet, token ring, Fiber Distributed Data Interface (FDDI), and/or other like network communications protocols). The NDE probe 100 may be configured to transmit or otherwise communicate the generated examination data to the one or more other hardware computing devices (e.g., NDE data acquisition device 580, computing system 500, and the like) via the network interface.

In some example embodiments, the NDE probe 100 may include memory, one or more processors, and/or other like hardware components. In such embodiments, the NDE probe 100 may be configured to generate examination data based on the detected, measured, and/or analyzed energy level of the signals penetrating the object, and transmit the examination data to a computing device (e.g., NDE data acquisition device 580 and/or computing system 500) to be encoded.

In various example embodiments, the NDE probe 100 may include one or more electro-mechanical components which allow the NDE probe 100 to change its position and/or orientation without being manually manipulated. These electro-mechanical components may include one or more motors, wheels, thrusters, propellers, claws, claps, hooks, and/or other like propulsion components. The NDE probe 100 may also be magnetized to allow the NDE probe 100 to magnetically attach to the examination object, particularly if the examination object is at least partially composed of ferrous material and/or material that may be magnetized. The NDE probe 100 may be configured to change its position and/or orientation based on a desired (or alternatively "predetermined") trajectory. Such a trajectory may be determined or otherwise defined by a human operator who determines where and how the NDE probe 100 is to reach various positions and/or orientations. In some embodiments, the NDE probe 100 may include an autonomous position and/or orientation changing mechanism, which allows the NDE probe 100 to change its current position and/or orientation based on knowledge of its current position and/or current orientation. The NDE probe 100 may be implemented as a semiautonomous or autonomous robot, or the like, configured to traverse the examination object. Knowledge of the current position and/or current orientation may be calculated by one or more sensors such as motor encoders, vision, stereopsis, lasers, and/or global positioning systems (GPS). Knowledge of the current position and/or current orientation may also be transmitted to the NDE probe 100 by the computing system 500, where the computing system 500 may determine the current position and/or current orientation of the NDE probe 100 based on a current position and/or current orientation of the SSFOC 200.

In various example embodiments, the shape sensing fiber optic cable NDE examination data encoding system may further include a SSFOC 200 that may be affixed or removably attached to the NDE probe 100. The opposite end of the SSFOC 200 may also be affixed or removably attached to a shape sensing device 400. The SSFOC and the shape sensing device 400 may be configured to determine a position and/or orientation of an object, such as the NDE probe 100, and convert the sensed position and/or orientation into a signal and/or data stream which can be read by a computing device (e.g., computing system 500). In various example embodiments, shape sensing device 400 may be configured to record and/or store the sensed position and/or orientation as position information and/or orientation information (or alternatively "position data" and/or "orientation data"). Once the position information and/or orientation information is sensed and recorded, such position information and/or orientation information may be reported or otherwise transmitted to a computing system (e.g., computing system 500) to be encoded (i.e., correlated with obtained examination data) and/or stored on a data storage device. NDE probe 100 and/or shape sensing device 400 may also be configured to receive data requests and/or control data from one or more computing devices (e.g., computing system 500). The SSFOC 200 and shape sensing device 400 will be described in greater detail in connection with FIG. 3.

According to various example embodiments, computing system 500 is a physical hardware computing device capable of communicating with a one or more other hardware computing devices (e.g., NDE probe 100, shape sensing device 400, NDE data acquisition device 580, one or more associated databases (not shown), and the like) via a communications interface, such that computing system 500 is able to receive one or more signals and/or data streams from the other hardware computing devices. Computing system 500 may include memory and one or more processors. Computing system 500 may be designed to sequentially and automatically carry out a sequence of arithmetic or logical operations; equipped to record/store data on a machine readable medium; and transmit and receive data via one or more network devices. Computing system 500 may include devices such as desktop computers, laptop computers, a mobile terminal (e.g., tablet personal computers and the like), and/or any other physical or logical device capable of recording, storing, and/or transferring digital data via a connection to a network device.

In various example embodiments, computing system 500 may include a network interface configured to connect computing system 500 to one or more other hardware computing devices (e.g., NDE probe 100, shape sensing device 400, NDE data acquisition device 580, one or more associated databases (not shown)) wirelessly via a transmitter and a receiver (or optionally a transceiver) and/or via a wired connection using a communications port. Computing system 500 may be configured to send/receive data to/from one or more other hardware computing devices (e.g., NDE probe 100, shape sensing device 400, NDE data acquisition device 580, one or more associated databases (not shown)), and/or network devices, such as a router, switch, or other like network devices, via the network interface using the wired connection and/or the wireless connection. The wireless transmitter/receiver and/or transceiver may be configured to operate in accordance with the IEEE 802.11-2007 standard (802.11), the Bluetooth standard, and/or any other like wireless standards. The communications port may be configured to operate in accordance with a wired communications protocol, such as a serial communications protocol (e.g., the Universal Serial Bus (USB), FireWire, Serial Digital Interface (SDI), and/or other like serial communications protocols), a parallel communications protocol (e.g., IEEE 1284, Computer Automated Measurement And Control (CAMAC), and/or other like parallel communications protocols), and/or a network communications protocol (e.g., Ethernet, token ring, Fiber Distributed Data Interface (FDDI), and/or other like network communications protocols). Computing system 500 may be configured to "encode" or otherwise correlate position and/or orientation information received from the shape sensing fiber optic cable with examination data received from one or more NDE probes. Additionally, the computing system 500 may be incorporated into a semiautonomous or autonomous electro-mechanical device and/or robot.

According to various example embodiments, object 600 may be any object, material, component, and/or system that may undergo an examination. For example, object 600 may be a pipe, an engine or frame, an airframe, a space frame, propeller, pressure vessel, storage tank, a boiler, a heat exchanger, a turbine bore, in-plant piping, inspection equipment, tubing material, a rail, a beam, and/or one or more components thereof. The object 600 may also be a fossil, an archaeological specimen, or the like. Object 600 may be made of one or more natural and/or synthetic materials. Additionally, object 600 may include one or more components that are welded together. Object 600 may be associated with one or more American Society of Mechanical Engineers (ASME) code and/or standard. ASME codes include a set of technical definitions and guidelines that address safety, design, construction, installation, operation, inspection, testing, maintenance, alteration, and repair of various components in a mechanical system. In various example embodiments, one or more ASME codes associated with object 600 may be used by the shape sensing fiber optic cable NDE examination data encoding system to determine a desired examination protocol, including a signal strength required for performing an examination.

As shown in FIG. 1, only one NDE probe 100, SSFOC 200, NDE probe cable 300 and NDE data cable 310, shape sensing device 400, computing system 500 and NDE data acquisition device 580 are present. However, according to various example embodiments, any number of NDE probes, SSFOCs, NDE probe data cables, shape sensing devices, NDE data acquisition devices and/or computing systems. Additionally, in various example embodiments, NDE probe 100, shape sensing device 400, NDE data acquisition device 580 and/or computing system 500 may be wirelessly networked devices, with NDE probe cable 300 and NDE data cable 310 omitted from the configuration of the NDE examination data encoding system. Alternatively, in various example embodiments, the NDE probe 100, shape sensing device 400, NDE data acquisition device 580 and/or computing system 500 may be provided as a single device.

Figure 2:
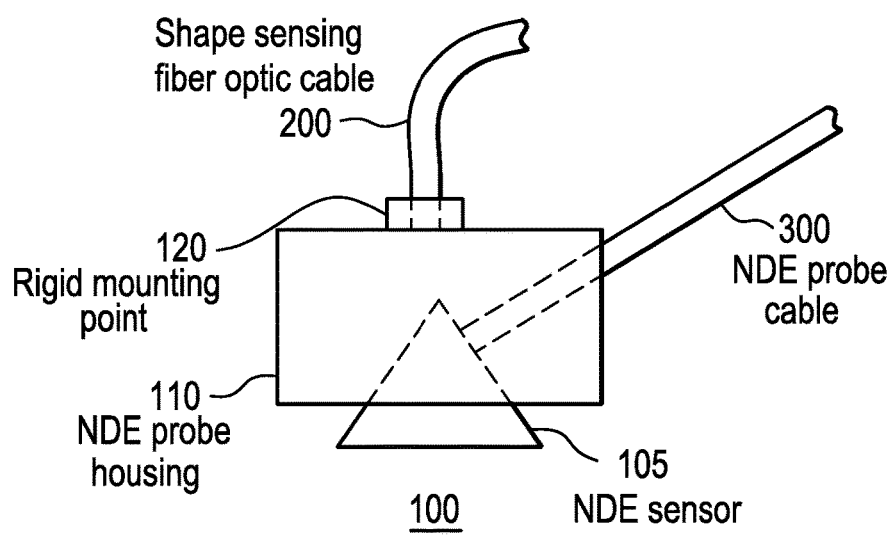
FIG. 2 illustrates the components of an NDE probe that may be employed by the system for encoding examination data of an object of FIG. 1, according to an example embodiment.

Referring now to FIG. 2, FIG. 2 illustrates an NDE probe 100, according to an example embodiment. The NDE probe 100 may include one or more sensors 105 that may be configured to perform an examination of object 600 by transmitting signals into object 600 and obtaining return or echo signals. In various example embodiments, the NDE probe 100 may include a sensor, device, and/or other like materials which senses vibrations created by the return or echo signals (e.g., piezoelectric crystal materials, such as gallium phosphate, quartz, tourmaline, Lead Magnesium Niobate-Lead Titanate (PMN-PT), and the like). The NDE probe 100 may convert the vibrations created by the return or echo signals into an electrical signal and/or radio signal, which may be transmitted to the NDE data acquisition device 580. The NDE data acquisition device 580 may then use the received signals to determine characteristics of the object 600, such as the position and/or orientation of an incident (e.g., a crack or fissure) within the object 600. The NDE data acquisition device 580 may determine the distance to an incident within the object 600 based on the known properties of the object 600 (e.g., size, shape, material, and the like) and/or other like criteria. In various example embodiments, the NDE data acquisition device 580 may produce, based on the received signal, a waveform, image, or other like visual and/or data representation which represents the signals and the return or echo signals moving through object 600. The visual and/or data representation may be a two-dimensional or a three-dimensional representation of the signals moving through object 600. The NDE data acquisition device 580 may then transmit the visual and/or data representation of the signals moving through object 600 to the computing system 500 for encoding with the position and/or orientation information obtained by the shape sensing device 400. The NDE data acquisition device 580 may also be incorporated into the computing system 500.

In some embodiments, the NDE probe 100 may include at least one processor and/or a sensor (not shown). The processor and/or sensor within the NDE probe 100 may calculate a time interval between transmitting the signals and receiving the return or echo signals. The calculated time interval may then be sent to NDE data acquisition device 580 and/or computing system 500 as examination data, where the NDE data acquisition device 580 and/or computing system may determine characteristics of the object 600 based on the calculated time interval. The signals may penetrate through object 600 without reflecting off any intermediary objects or other like articles. Thus, object 600 depicted in FIG. 1 may not have an indication of a deficiency (e.g., a crack or fissure).

According to various example embodiments, the NDE probe may be configured to perform examinations using, for example, ultrasonic testing (UT), eddy-current testing (ECT), acoustic emission testing (AE), electromagnetic testing (ET), laser testing methods (LM), leak testing (LT), magnetic flux leakage (MFL), liquid penetrant testing (PT), magnetic particle testing (MT), neutron radiographic testing (NR), radiographic testing (RT), thermal/infrared testing (IR), vibration analysis (VA), visual testing (VT), remote visual inspection (RVI), low coherence interferometry (LCI), or other similar examination techniques.

Referring back to FIG. 2, the NDE probe 100 may further include a housing 110, and the housing may include a rigid mounting point 120. The SSFOC 200 may be affixed or removably attached to the rigid mounting point 120. The rigid mounting point 120 may be configured to connect the SSFOC 200 to the housing 110 of the NDE probe 100 so that the SSFOC 200 does not slip and/or move during the course of an examination. Further, the rigid mounting point 120 is of a known distance from the surface of the NDE sensor 105 that comes into contact with the object 600, thereby allowing the shape sensing device 400 to calculate and/or determine the position of the NDE probe 100 on the surface of the object 600, based in part on the known distance and information regarding the dimensions of the probe housing.

In various embodiments, the NDE probe 100 may include a network interface configured to connect NDE probe 100 to one or more other hardware computing devices (e.g., NDE data acquisition device 580, computing system 500) wirelessly via a transmitter and a receiver (or optionally a transceiver) and/or via a wired connection (e.g., NDE probe cable 300 and NDE data cable 310) using a communications port. NDE probe 100 may be configured to send/receive data to/from one or more other hardware computing devices (e.g., NDE data acquisition device 580 and/or computing system 500), and/or network devices, such as a router, switch, or other like network devices, via the network interface using the wired connection and/or the wireless connection. The wireless transmitter/receiver and/or transceiver may be configured to operate in accordance with the IEEE 802.11-2007 standard (802.11), the Bluetooth standard, and/or any other like wireless standards. The communications port may be configured to operate in accordance with a wired communications protocol, such as a serial communications protocol (e.g., the Universal Serial Bus (USB), FireWire, Serial Digital Interface (SDI), and/or other like serial communications protocols), a parallel communications protocol (e.g., IEEE 1284, Computer Automated Measurement And Control (CAMAC), and/or other like parallel communications protocols), and/or a network communications protocol (e.g., Ethernet, token ring, Fiber Distributed Data Interface (FDDI), and/or other like network communications protocols).

Figure 3:
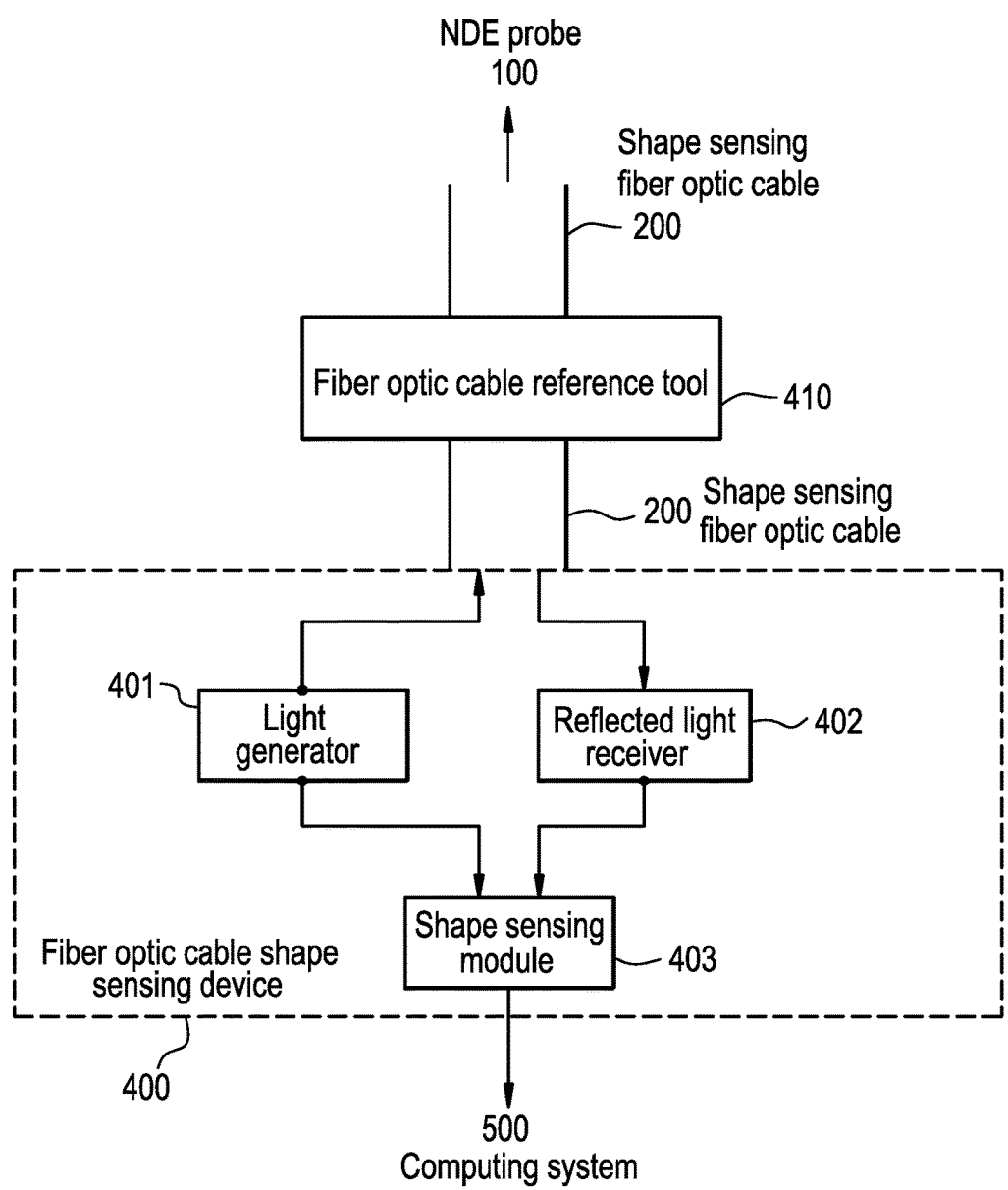
FIG. 3 illustrates the components of a fiber optic cable shape sensing device that may be employed by the system for encoding examination data of an object of FIG. 1, according to an example embodiment.

Referring now to FIG. 3, while the examination is being performed by the NDE probe 100, the shape sensing device 400 may sense a position and orientation of the SSFOC 200, which is affixed and/or removably attached to NDE probe 100. The SSFOC 200 may also be affixed and/or removably attached to a fiber optic cable reference tool ("reference tool") 410, which may be then be connected to the NDE probe 100 with a SSFOC.

In order to determine and/or calculate the position of the NDE probe 100, a frame of reference should be established and the shape sensing equipment (e.g., shape sensing device 400 and/or reference tool 410) should be secured and/or braced so that the beginning of the SSFOC 200 does not move during the examination because the position and/or orientation information collected from the SSFOC 200 may be relative to the beginning position and/or orientation of the SSFOC 200. When the examination begins, the reference tool 410 may be placed, affixed and/or attached to a reference point that has a known location that may provide a frame of reference for position and/or orientation information collected from the SSFOC 200. The reference point may be located on the examination object 600, such as the top dead center of a pipe's weld centerline. The reference tool 410 may also have an NDE probe alignment interface (not shown) that aligns the NDE probe 100, and by extension the SSFOC 200 that is attached and/or affixed to the NDE probe 100, with a known location relative to the reference tool 410 and may act as a starting location and/or orientation point for the examination of the object 600.

Once the NDE probe 100 is aligned with the reference tool 410, the encoding software operating on the computing system 500 may be notified that the NDE probe 100 is in its starting location and/or orientation point ("starting point"). This starting point may be referenced for the rest of the examination of the object 600 for as long as the reference tool 410 is positioned at the reference point. In situations where it may be desirous for the shape sensing equipment to be repositioned during an examination of an object 600, the reference tool 410 may be relocated to another known location, possibly on the object 600, and the examination may be continued from the second known reference point after notification is transmitted to the encoding software operating on the computing system 500. In various example embodiments, the reference point may be based on a desired starting point, for example, when the current examination is a replication and/or duplication of an earlier conducted examination. The starting point may be a first point on object 600 from which examination data is obtained by the computing system 500. It should be noted that other points from which examination data is obtained by the computing system 500 may be referred to as "examination points" and the starting point may also be referred to as a "first examination point".

Additionally, the starting point is defined in order to produce consistent and/or comparable data sets when multiple examinations are conducted on a given object. Thus, the determining of a starting point may be useful for properly correlating the examination data with the position and/or orientation of the shape sensing fiber optic cable NDE examination data encoding system. In typical examination protocols (e.g., manual examinations and/or automatic examinations), a human operator may make various measurements and computations in order to determine a reference point and/or a starting point. However, when replicating and/or duplicating an examination, human error in determining a reference point and/or a starting point may result in less consistent and/or less comparable data sets when multiple examinations are conducted on a given object.

In other example embodiments, a reference point and/or a starting point may be determined without the use of a reference tool. In such embodiments, the shape sensing device 400 may also perform the functionality of the reference tool 410. The shape sensing device 400 may be used by computing system 500 to define the reference point based on a chosen and/or desired two-dimensional (2D) or 3D plane on or off the object 600. The computing system 500 may determine the reference point by scanning a desired portion of the object 600, defining a plane based on scanned portion, and determining the reference point based on the scanned portion of the plane. In various example embodiments, the plane may be defined using at least three points on a desired portion of the object 600. In other example embodiments, the plane may be defined using at least three points at a desired area off of the object 600. Scanning the desired area may be based on one or more criteria of the object, such as a geometry of the object 600 (i.e., a size, shape, circumference, radii, diameter, and the like), one or more materials used in the construction and/or manufacture of the object 600, a position and/or orientation of the object 600, an environment in which the object 600 is located, dimensions of the area that the object 600 is located in, and/or other like criteria. Once the reference point is determined, the shape sensing device 400 may be placed in the determined reference point, and the starting point and/or the first examination point may be determined.

In various example embodiments, the shape sensing device 400 may capture and/or record the shape of the SSFOC 200 attached to the NDE probe 100 and may calculate and/or otherwise determine the position and/or orientation of the NDE probe 100 based on the shape of the SSFOC 200. The shape sensing device 400 may include a light generator 401, a reflected light receiver 402, and/or a shape sensing module 403.

Figure 4:
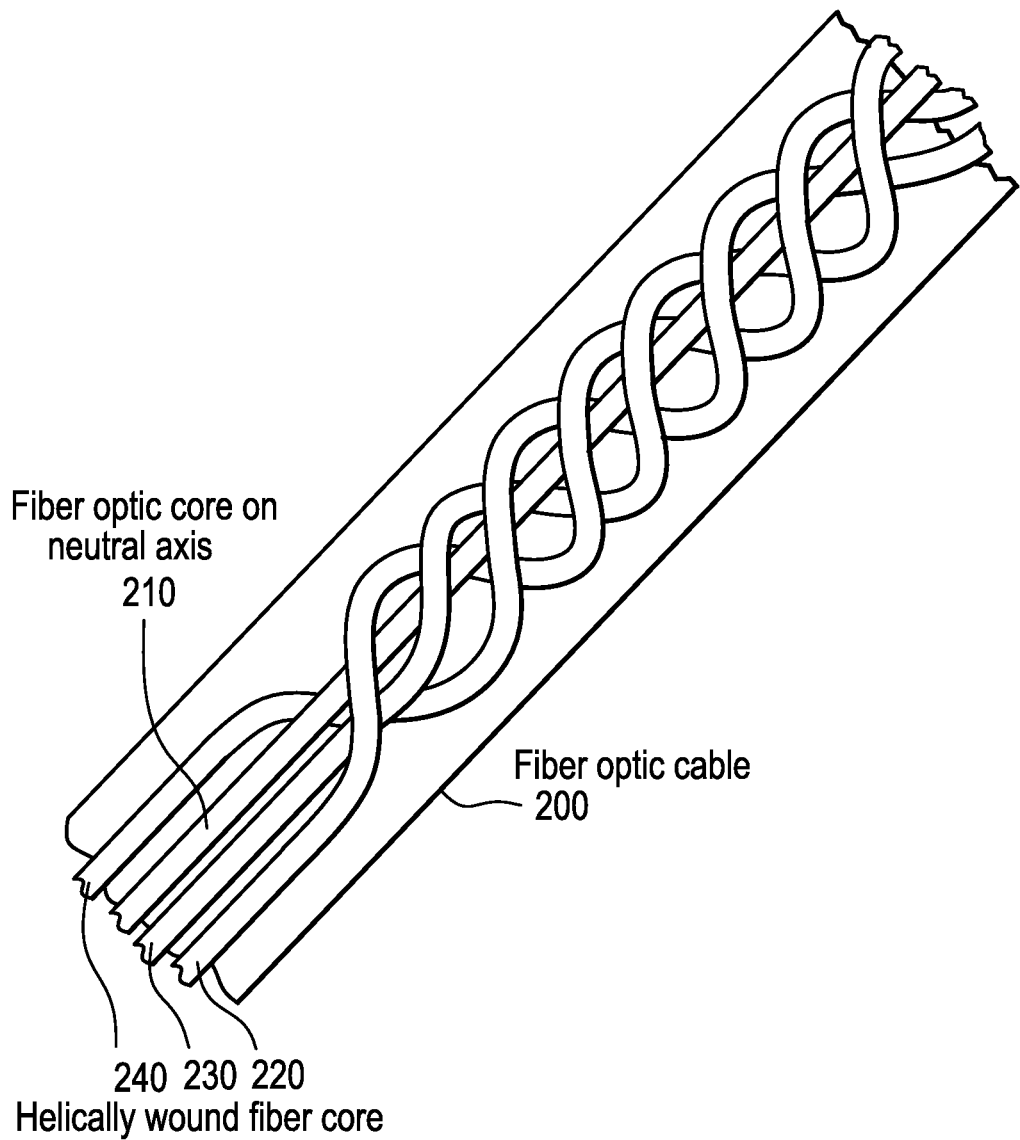
FIG. 4 illustrates the components of a shape sensing fiber optic cable that may be employed by the system for encoding examination data of an object of FIG. 1, according to an example embodiment.

Referring to FIG. 4, FIG. 4 illustrates a shape sensing fiber optic cable 200 according to an example embodiment. The SSFOC 200 may include one or more fiber optic cores (210, 220, 230, and 240). The SSFOC 200 may include a fiber optic core on a neutral axis 210, and one or more helically wound fiber optic cores (e.g., 220, 230, and 240) that may be wound around the neutral axis 210. In various example embodiments, the SSFOC 200 may be affixed, connected, and/or attached to the NDE probe 100, the reference tool 410, and/or the shape sensing device 400. The light generator 401 of the shape sensing device 400 may be configured to generate and emit light of a desired frequency through the SSFOC 200. If the SSFOC 200 is bent, curved, twisted, deformed, or the like, the fiber optic core(s) of the SSFOC 200 will be subjected to tensional force and/or compressional forces from the deformation of the SSFOC 200. These forces will change the optical properties of one or more of the fiber cores due to the induced strain. The strain on the fiber optic core 210 may be quantified by analyzing the light passing through the fiber optic core 210, e.g., the light generated by light generator 401, and comparing the frequency of the light that passed through the fiber optic core with the frequency of the light reflected back to the shape sensing device 200, which was received by the reflected light receiver 402. In various example embodiments, the shape sensing module 403 will compare the frequency of the light generated by the light generator 401 with the frequency of the reflected light received by the reflected light receiver 402, and may determine the location and amount of strain, if any, the SSFOC 200 is under based on the comparison of the two lights. Comparison of the location and the magnitude of strain in one or more cores determines the change in shape of the SSFOC 200.

In other example embodiments, the SSFOC 200 may include a plurality of fiber optic cores (e.g., 220, 230, and 240) that may be helically wound around a neutral axis fiber optic core (210). While FIG. 4 depicts three helically wound fiber optic cores, other example embodiments may contain more or less fiber optic cores. Additionally, while FIG. 4 depicts the fiber optic cores arranged in a helical configuration around the neutral axis fiber optic core 210, other fiber optic core configurations may be used as well to the same effect, such as using a triangular, polygonal, or other like geometrically shaped configuration, using one or more fiber optic cores in an interlocked configuration, or other like configuration. Additionally, the fiber optic cores may have internal partitions that segment the fiber optic core along the fiber optic core's axis, thereby providing similar effect in a single fiber optic core as would be provided in a plurality of fiber optic cores. With the helically wound fiber optic cores 220, 230, and 240 the additional fiber optic cores may provide additional measurements of strain on the SSFOC 200 (i.e., tension and compression forces on the fiber optic cores), thereby providing additional information from which the shape sensing device 400 and/or computing system 500 may determine the curvature of the SSFOC 200. Additionally, the fiber optic cores (e.g., 210, 220, 230 and 240) may include fiber Bragg gratings. Bragg gratings are a type of Bragg reflector that may be doped into the SSFOC, thereby changing the refractive index of the fiber optic glass and can be tuned to reflect specific wavelengths of light and transmit all others. The Bragg gratings may be fabricated throughout the entire length of the fiber optic core(s). When light is generated by the light generator 401 that is matched to the frequency of the Bragg gratings and transmitted through the SSFOC 200, the Bragg gratings within the fiber optic core(s) of SSFOC 200 will reflect their originally tuned frequency of light if they are in an unstrained state (i.e., there is no tension and/or compression on the fiber optic core(s)). However, if the SSFOC 200, and the Bragg gratings within the SSFOC 200, is under a strain, the Bragg gratings will reflect a different frequency of light that corresponds to the amount of strain that the fiber optic cores of the SSFOC 200 is under. In other words, if the SSFOC is under strain, there may be a detectable phase change in the light reflected by the SSFOC. The reflected light may be transmitted to the reflected light receiver 402 and then compared to the emitted light generated by the light generator 401 by the shape sensing module 403. The shape sensing module 403 may then determine the shape of the SSFOC 200 with high accuracy.

In other example embodiments, the Bragg gratings of the fiber optic core(s) of the SSFOC 200 may be tuned to reflect different frequencies of light. Additionally, the light generator 401 may be configured to emit frequency modulated light, thereby emitting into the SSFOC 200 light that varies in frequency. Using the principle discussed above, the Bragg gratings, if under strain, will reflect the varying frequencies of light emitted by the light generator 401 at a different frequency of light to the reflected light receiver 402. Using this data, the shape sensing module 403 may then determine the shape of the SSFOC 200 with high accuracy.

By determining whether the SSFOC 200 is under strain, determining the curvature of the fiber optic cores based on the analysis of the strain data of the SSFOC 200, the curvature(s) of the SSFOC 200 and the distance in the SSFOC 200 where the curvature(s) is seen may be determined. From the determined curvature and distance information of the SSFOC 200, the distance, position, and orientation information of the NDE probe 100 may be determined because the end point of the SSFOC 200 is known to be affixed, connected and/or attached to the rigid mounting point 120 of the NDE probe 100. Further, the distance, position and orientation information may be calculated for a two-dimensional or three-dimensional space, relative to the determined reference point and/or starting point discussed above.

While the example embodiments have been discussed as using Bragg gratings to determine the shape of a SSFOC, other techniques of determining the shape of a SSFOC may be used as well. For example, the use of the Rayleigh scattering effect may be used to determine the shape of a SSFOC. The Rayleigh scattering effect refers to the optical phenomenon where light and other sources of electromagnetic radiation may be dispersed or scattered by particles that have a radius of less than about ¹/₁₀ of the wavelength of the radiation, and the angle at which the radiation (i.e., light) is scattered varies inversely as the fourth power of the wavelength of the radiation. When using the Rayleigh scattering effect to determine the shape of a SSFOC, a reference Rayleigh back scatter pattern may be determined by transmitting light through the fiber optic core(s) of the SSFOC (and/or segments of the fiber optic core(s) of the SSFOC) in an unstrained state. Because the Rayleigh back scatter pattern of the fiber optic core(s) of the SSFOC is directly dependent on the unique composition of the fiber optic core(s) (due to variations of density and refractive index in the silica glass fibers that are used in the construction of the fiber optic core(s)), the Rayleigh back scatter pattern for the SSFOC is fixed at the time of the manufacture of the SSFOC. Therefore, once a reference Rayleigh back scatter pattern is determined, that pattern may be used to determine the amount of strain, and the location of the strain, that the SSFOC is under by comparing the measured Rayleigh back scatter pattern after light from the shape sensing device is transmitted through the SSFOC to the reference Rayleigh back scatter pattern.

Once the shape sensing device 400 determines the shape of the SSFOC, the shape sensing device 400 may then send the position and orientation information of the NDE probe 100 to computing system 500 via a wired or wireless communication protocol. Computing system 500 may determine the position and/or orientation of the NDE probe 100 based on the received position and/or orientation information, and determine a position and/or orientation of a point where the examination data is being obtained (i.e., an examination point). Since FIG. 1 depicts the NDE examination system being placed in a determined starting position, the determined examination point should be substantially the same or substantially equivalent to the origin point and/or the first examination point. Once the examination point is determined, the computing system 110 encodes the examination data with the position and/or orientation information by correlating the examination data received from the NDE probe 100 with position and/or orientation information from the shape sensing device 400. The encoding of the examination data may occur in real-time, or may be encoded at a time after the NDE inspection by the operator has been completed.

Additionally, the encoded examination may be stored in a computer readable file format that is compatible with software that is used to view, display, print, or the like, two-dimensional and three-dimensional encoded examination data. Further, according to various embodiments, the file format of the encoded examination data may also support the viewing and/or displaying of the encoded examination data in real-time by a computing system, such as the computing system 500.

In various example embodiments, the shape sensing device 400 may also include a network interface (not shown) configured to connect the shape sensing device 400 to one or more other hardware computing devices (e.g., computing system 500) wirelessly via a transmitter and a receiver (or optionally a transceiver) and/or via a wired connection using a communications port. The shape sensing device 400 may be configured to send/receive data to/from one or more other hardware computing devices (e.g., computing system 500), and/or network devices, such as a router, switch, or other like network devices, via the network interface using the wired connection and/or the wireless connection. The wireless transmitter/receiver and/or transceiver may be configured to operate in accordance with the IEEE 802.11-2007 standard (802.11), the Bluetooth standard, and/or any other like wireless standards. The communications port may be configured to operate in accordance with a wired communications protocol, such as a serial communications protocol (e.g., the Universal Serial Bus (USB), FireWire, Serial Digital Interface (SDI), and/or other like serial communications protocols), a parallel communications protocol (e.g., IEEE 1284, Computer Automated Measurement And Control (CAMAC), and/or other like parallel communications protocols), and/or a network communications protocol (e.g., Ethernet, token ring, Fiber Distributed Data Interface (FDDI), and/or other like network communications protocols).

Figure 5:
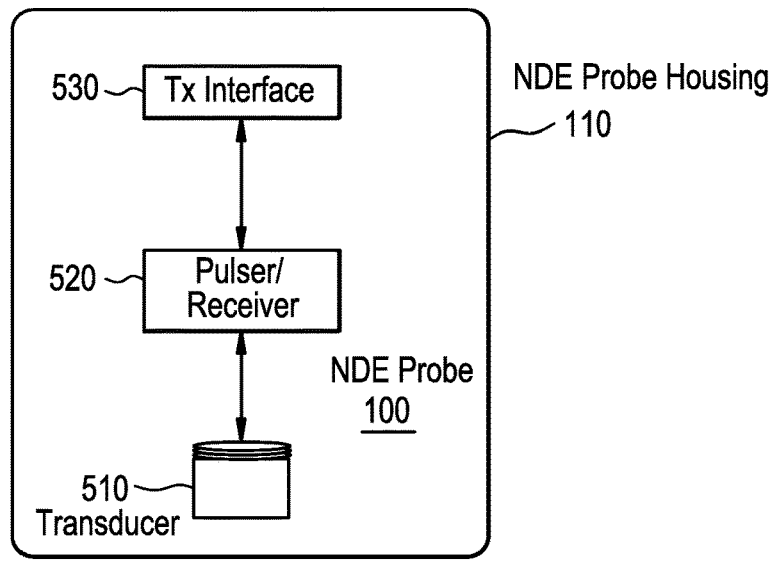
FIG. 5 illustrates the components of an ultrasonic transducer/receiver that may be employed by the NDE probe of FIG. 2, according to an example embodiment.

FIG. 5 illustrates the components of a NDE probe 100 that is employed by the NDE examination system, according to an example embodiment. As shown, the NDE probe 100 may include a housing 110, transducer 510, pulser/receiver 520, and transmission interface 530.

According to various example embodiments, housing 110 may be any device that is used to physically mount the NDE probe 100 to an object 600 and which is used to physically contain or otherwise include one or more components of the NDE probe 100 (e.g., transducer 510, pulser/receiver 520, and transmission interface 530). Housing 110 may be manufactured out of various materials and/or fibers, including metal, plastic, glass, rubber, and/or any other like materials that are natural and/or synthetic. In various example embodiments, housing 110 may be formed into various sizes and/or shapes based on one or more criteria of an examination object, such as a geometry of the examination object (i.e., a size, shape, circumference, radii, diameter, and the like), one or more materials used in the construction and/or manufacture of the examination object, a position and/or orientation of the examination object, an environment in which the examination object is located, and/or other like criterion. Furthermore, housing 110 may attach to an examination object by way or a couplant, such as oil, water, or other like couplant material. Using a couplant material may increase an efficiency of an examination by reducing losses in wave energy due to separation between a surface of the housing 110 and the surface of the examination object (e.g., object 600), imperfections, and/or other conditions in a space between the housing 110 and/or the transducer 520.

In some example embodiments, housing 110 may attach to an examination object using one or more attachment components (not shown) which allow the shape sensing device 400 and/or computing system 500 to attach to an examination object. In various example embodiments, the one or more attachment components may include a magnetic component (i.e., any material, or combinations of materials, that attracts other permanent magnetic materials and/or any ferromagnetic materials), an adhesive component (i.e., any substance applied to a surface of at least two materials that binds them together and resists separation), and the like. In various example embodiments, the one or more one or more attachment components may include one or more implements, such as hooks, clamps, fasteners, and the like. In various example embodiments, housing 110 may include one or more electro-mechanical components (not shown) which allow the shape sensing device 400 and/or computing system 500 to change its position and/or orientation. These electro-mechanical components may include one or more motors, wheels, thrusters, propellers, claws, claps, hooks, and/or other like propulsion components.

According to various example embodiments, transducer 510 may be any device that converts a signal in one form of energy to another form of energy. Energy types include (but are not limited to) electrical, electromagnetic (including light), chemical, acoustic, thermal energy, and the like. Transducer 510 may include the use of a sensor/detector, where the sensor/detector is used to detect a parameter in one form and report it in another form of energy. In such embodiments, the reporting form of energy may include an analog signal, a digital data stream, and the like. In various example embodiments, transducer 510 may generate and transmit signals into an examination object in a pulse-like fashion, and may receive of the pulsed waves that are reflected back to the NDE probe 100. The reflected signals may come from an interface, such as the back wall of the examination object or from an imperfection or deficiency within the object. In various example embodiments, transducer 510 may include a sensor, device, and/or other like material which senses vibrations created by the return or echo signals (e.g., piezoelectric crystal materials, such as gallium phosphate, quartz, tourmaline, Lead Magnesium Niobate-Lead Titanate (PMN-PT), and the like). The transducer 510 may convert the vibrations created by the return or echo signals into an electrical signal and/or radio signal, which may be transmitted to the computing system 500. The pulses of signals may be generated in accordance with pulser/receiver 520.

According to various example embodiments, pulser/receiver 520 may be any device that may control a timing and strength of energy generated and transmitted by a transducer (e.g., transducer 510). The pulser section of the pulser/receiver 520 may generate electric pulses of controlled energy, which are converted into pulses when applied to transducer 510. Control functions associated with the pulser section of the pulser/receiver 520 include pulse length or damping (i.e., the amount of time the pulse is applied to the transducer), and pulse energy (i.e., the voltage applied to the transducer). In various example embodiments, the pulser section of the pulser/receiver 520 may apply a desired amount of voltage to transducer 510 based on one or more criteria of an examination object, such as a geometry and/or shape of the object, a material and/or substance of the object, a position of the object in relation to one or more other objects, a location and/or environment in which the object is located, and/or other like criteria. The receiver section of the pulser/receiver 520 may receive signals produced by the transducer, which represent received or echoed signals, and convert the received or echoed signals produced by the transducer 510 into an analog signal or a digital signal to be transmitted via the transmission interface 530. In various example embodiments, receiver section of the pulser/receiver 520 may include a sensor, device, and/or other like material which senses vibrations created by the return or echo signals (e.g., piezoelectric crystal materials, such as gallium phosphate, quartz, tourmaline, Lead Magnesium Niobate-Lead Titanate (PMN-PT), and the like), and converts the sensed vibrations created by the return or echo signals into an electrical signal. In various example embodiments, the receiver section of the pulser/receiver 520 may perform signal rectification, filtering, gain and/or signal amplification, and the like.

According to various example embodiments, transmission interface 530 may be any electronic device that produces radio waves based on a received electrical signal. In various example embodiments, the transmission interface 530 may include an oscillator (not shown) to generate a radio frequency signal and a modulator (not shown) to add information or data to the generated radio frequency signal. In various example embodiments, transmission interface 530 may receive electrical signals from pulser/receiver 520, which represent the received or echoed signals produced by the transducer 510, and convert the electrical signals produced by the transducer 510 into a radio frequency signal to be transmitted to a computing device (e.g., computing system 500) via the transmission interface 530.

In various example embodiments, NDE probe 100 may include any number of transducers, pulser/receivers, and/or transmission interfaces. Furthermore, NDE probe 100 may include many more components than are not shown in FIG. 5, such as one or more processors and/or computer-readable storage devices.

Figure 6:
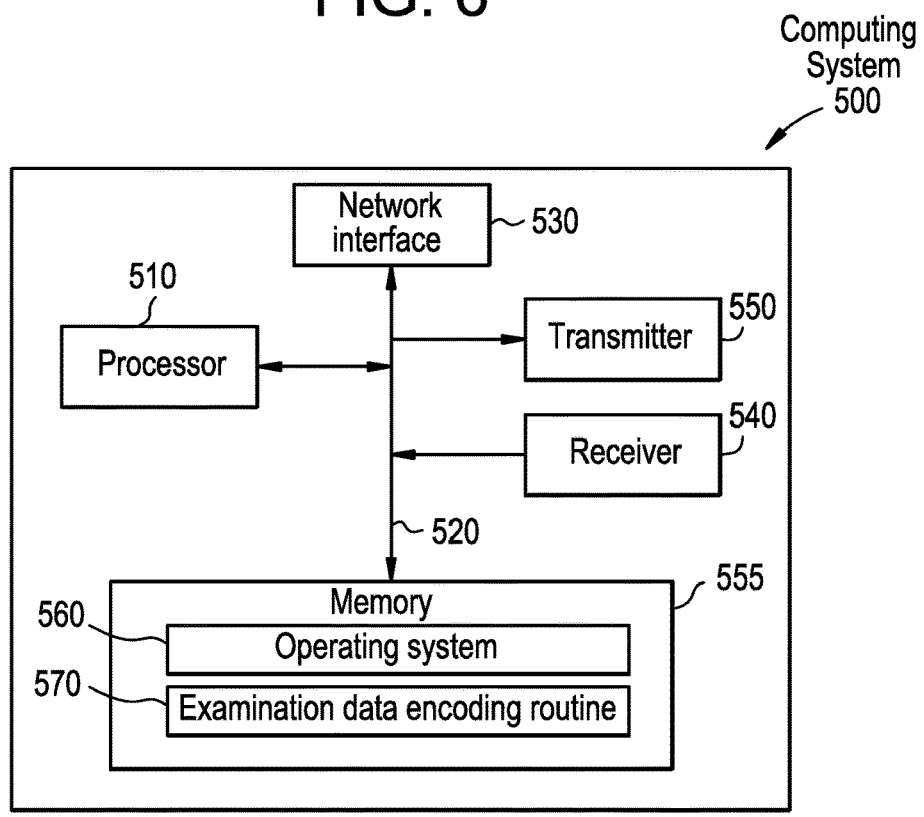
FIG. 6 illustrates the components of a computing system that may be employed by the system for encoding examination data of an object of FIG. 1, according to an example embodiment.

FIG. 6 illustrates the components of a computing system 500 that may be employed by the NDE examination data encoding system, according to an example embodiment. As shown, computing system 500 includes processor 510, bus 520, network interface 530, receiver 540, transmitter 550, and memory 555. During operation, memory 555 includes operating system 560 and examination data encoding routine 570. In some example embodiments computing system 500 may include many more components than those shown in FIG. 6, such as a display device and/or other like input/output devices. However, it is not necessary that all of these generally conventional components be shown in order to disclose the example embodiments.

Memory 555 may be a computer readable storage medium that generally includes a random access memory (RAM), read only memory (ROM), and a permanent mass storage device, such as a disk drive. Memory 555 also stores operating system 560 and examination data encoding routine 570. Additionally, memory 555 may include program code for booting, starting, and/or initializing the computing system 500. These software components may also be loaded from a separate computer readable storage medium into memory 555 using a drive mechanism (not shown). Such separate computer readable storage medium may include a floppy drive, disc, tape, DVD/CD-ROM drive, memory card, thumb drive, and/or other like computer readable storage medium (not shown). In some embodiments, software components may be loaded into memory 555 from a remote data storage device (not shown) via network interface 530, rather than via a computer readable storage medium.

Processor 510 may carry out instructions of a computer program by performing basic arithmetical, logical, and input/output operations of the system. Instructions may be provided to processor 510 by memory 555 via bus 520. Processor 510 is configured to execute program code for examination data encoding routine 570. Such program code may be stored in a storage device (e.g., memory 555).

Bus 520 enables the communication and data transfer between the components of computing system 500. Bus 520 may comprise a high-speed serial bus, parallel bus, storage area network (SAN), and/or other suitable communication technology.

Network interface 530 is a computer hardware component that connects computing system 500 to the other devices in the NDE examination data encoding system. Network interface 530 is configured to receive one or more input signals from one or more input devices and output one or more output signals to one or more instruments and/or components. Network interface 530 may connect computing system 500 to other instruments via an optical, wired, and/or wireless connection.

Receiver 540 may be any type of hardware device that can receive and convert a signal from a modulated radio wave into usable information, such as data and/or video. Receiver 540 may be coupled with an antenna (not shown) in order to capture radio waves. Receiver 540 may be configured to send data converted from a captured radio wave to one or more other components of computing system 500 via bus 520.

Transmitter 550 may be any type of hardware device that may generate, or otherwise produce, radio waves in order to communicate with one or more other devices. Transmitter 550 may be coupled with an antenna (not shown) in order to transmit data to one or more other devices. Transmitter 550 may be configured to receive digital data from one or more components of computing system 500 via bus 520, and convert the received digital data into an analog signal for transmission over an air interface. In various example embodiments, a transceiver (not shown) may be included with computing system 500. A transceiver may be a single component configured to provide the functionality of transmitter 550 and receiver 540 as discussed above.

Figure 7:
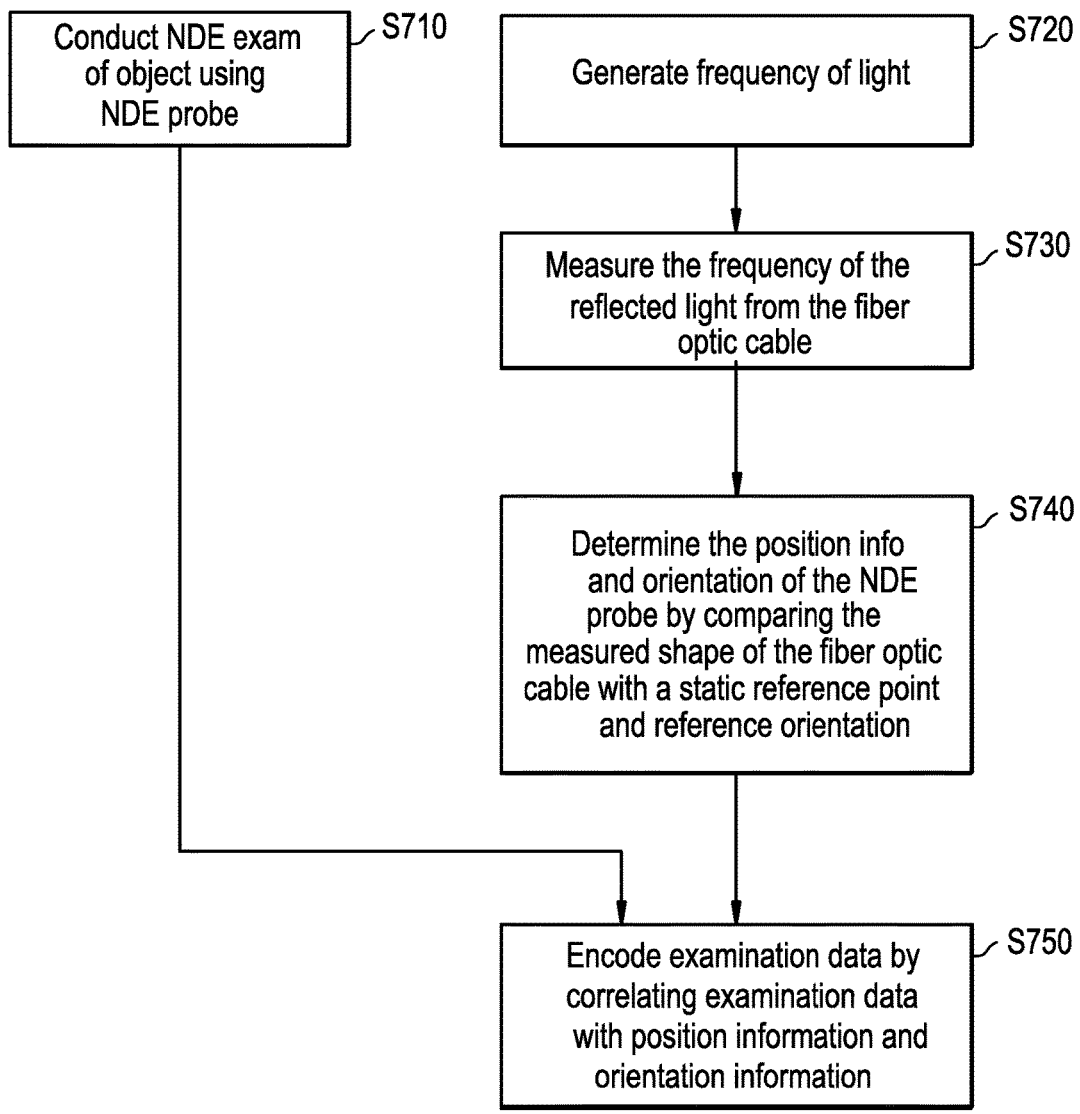
FIG. 7 illustrates a fiber optic shape sensing routine, according to an example embodiment.

FIG. 7 illustrates an examination data encoding routine 570, according to an example embodiment. Examination data encoding routine 570 may be used to encode or otherwise correlate examination data obtained from an NDE examination system with position information and/or orientation information obtained from one or more NDE probes (e.g., 100). For illustrative purposes, the operations of examination data encoding routine 570 will be described as being performed by computing system 500 in conjunction the other devices as illustrated in FIGS. 1-2. However, it should be noted that any computing device may operate the examination data encoding routine 570 as described below.

Referring to FIG. 7, as shown in operation S710, the NDE probe 100 may be utilized to conduct a NDE examination of an examination object, such as object 600. In operation S720, a light generator 401 may generate a desired frequency of light to be emitted to a SSFOC 200. In operation S730, a reflected light receiver 402 may measure the frequency of reflected light from a fiber optic cable, such as SSFOC 200. In operation S740, a shape sensing module 403 may determine the position information and orientation information of the NDE probe 100 by comparing the measured shape of the fiber optic cable with a static reference point and static reference orientation. In operation S750, the computing system 500 may encode the examination data received form the NDE probe 100 by correlating the examination data with position information and/or orientation information from the SSFOC 200. For example, the computing system 500 may perform the correlation synchronizing and/or mapping the examination data stream from the NDE probe 100 (via the NDE data acquisition device 580) with the measured position and orientation data stream from the shape sensing device 400 through the use of a master clock signal (not shown) sent to all of the devices of the NDE examination system, or by using synchronized clocks within the NDE probe 100 and the shape sensing device 400 and having the examination data stream and position and orientation data stream be time stamped using the synchronized clocks.

Figure 8:
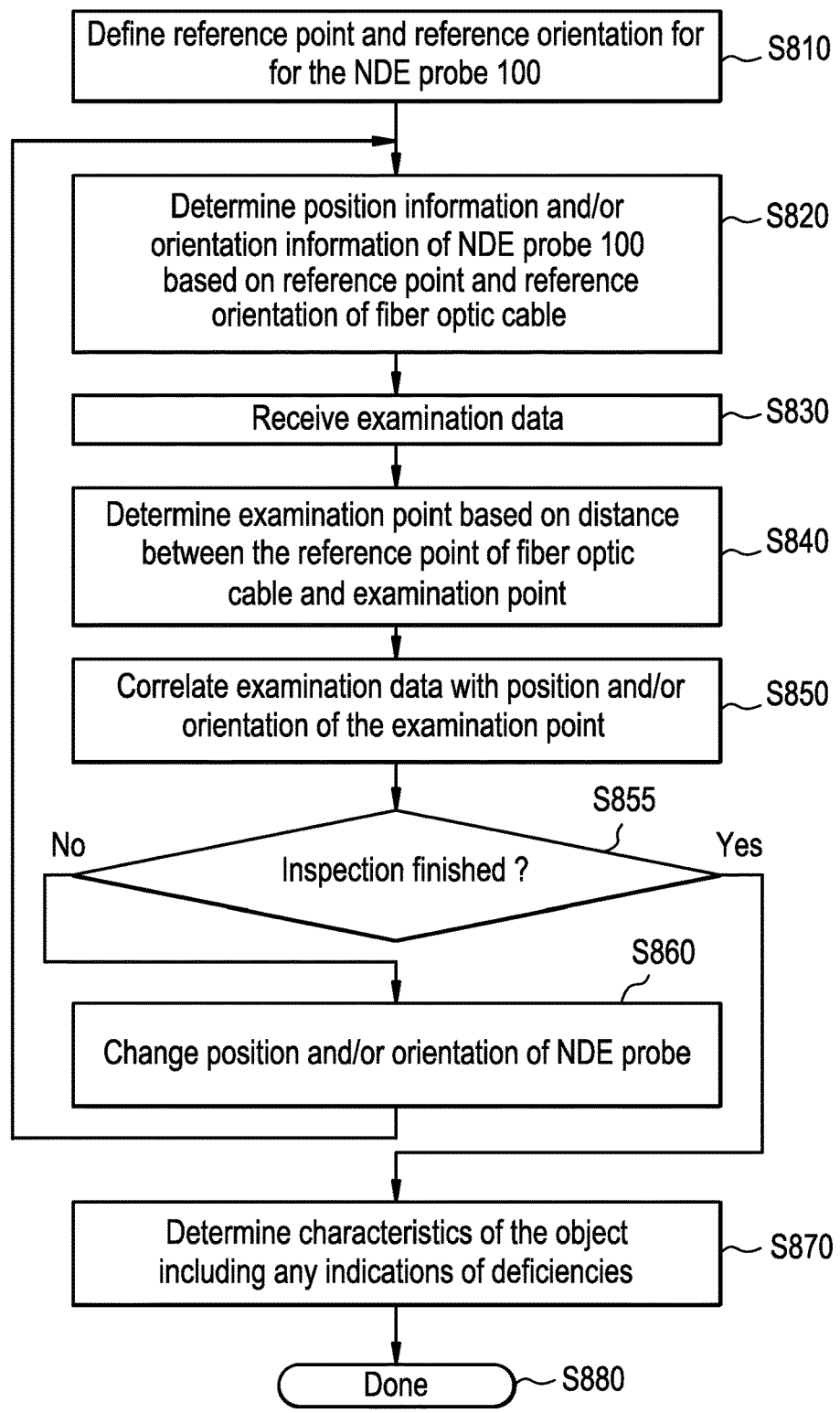
FIG. 8 illustrates an examination data encoding routine, according to an example embodiment.

Referring to FIG. 8, as shown in operation S810, the computing system 500 defines a reference point and reference orientation (i.e., starting point and starting orientation) of the NDE probe 100. The reference point and reference orientation is the first position and orientation of the NDE probe 100 prior to obtaining examination data. The reference point/orientation may be based on a desired starting position/orientation or may be any chosen position/orientation of the NDE probe 100. The reference point/orientation may be defined using a reference tool such as, reference tool 410 as described above with respect to FIG. 3.

As shown in operation S810, the computing system 500 defines a reference point and reference orientation based on the starting position. The reference point may be a first point on object 600 from which examination data is obtained by the NDE probe 100. As shown in operation S820, the computing system 500 determines position information and/or orientation information of the NDE probe 100 based on the reference point and/or orientation of the SSFOC 200. The computing system 500 may use one or more sensors (e.g., 105, 510) to sense, capture, measure, or otherwise collect position and/or orientation information from the NDE probe 100 using the reference point and/or orientation of the fiber optic cable, the shape sensing device 400 and the SSFOC 200.

As shown in operation S830, the computing system 500 receives examination data from the NDE probe 100. As discussed above, the NDE probe 100 may generate and transmit signals into an examination object (e.g., object 600) in a pulse-like fashion, receive the pulsed waves that are reflected back to the NDE probe 100, and transmit the received pulsed waves as a radio signal. In operations S830, the NDE data acquisition device 580 and/or computing system 500 may receive the radio signal generated by the NDE probe 100.

As shown in operation S840, the computing system 500 determines an examination point based on the shape of the SSFOC 200 and the reference point and reference orientation of the NDE probe 100. As shown in operation S850, the computing system 500 encodes the examination data by correlating the received examination data with the position and/or orientation of the examination point. Correlating the received examination data with the position and/or orientation of the examination point may include defining a relationship or otherwise associating the received examination data with the position information and/or orientation information, including correlating the examination data with the position and/or orientation information based on a common time and/or clock signal shared by the NDE probe 100, the shape sensing device 400, the NDE data acquisition device 580 and the computing system 500. For example, the correlation of the received examination data with the position and orientation of the examination point may include determining the time at which an examination data point was captured and then associating that examination data point with the position information and orientation information captured at that same time. It should be noted that the data streams coming from NDE probe 100 may vary depending on connection type. Additionally, the encoded examination may be stored in a computer readable file format that is compatible with software used to view, display, print, or the like, two-dimensional and three-dimensional encoded examination data. Further, according to various embodiments, the file format of the encoded examination data may also support the viewing and/or displaying of the encoded examination data in real-time by a computing system, such as the computing system 500.

For example, where ultrasonic testing is used, the examination data may be transmitted to the computing system 500 at an adjustable rate of ten bit packets per second, which is translated into numerical characteristic information of the object 600. The computing system 500 may produce or otherwise generate encoded data by time stamping the examination data, and associating the time stamped examination data with the determined position and/or orientation of the examination point. The encoded data may include depth, position information and/or orientation information, and the time to within one ten thousandth of a second based on the adjustable rate of ten bit packets per second. For added functionality, there may be a video camera employed in the NDE inspection system, e.g., attached to the NDE probe housing or operated by the human operator conducting the NDE examination, and the computing system 500 may capture the video data and synchronize it to the incoming examination data, which may act as a validation for the examination data collection process.

In various example embodiments, encoding the examination data may include may match and/or synchronize the received examination data with the position and/or orientation of the examination point. Thus, in various example embodiments, the computing system 500 may be configured to deal with transmission delay (i.e., "latency") or other like timing issues in relation to receiving the examination data or the position and/or orientation of the examination point. For example, in various example embodiments, the NDE probe 100 may be configured to send examination data to the computing system at a rate of 30 data points per second, or a frequency of 30 Hz. However, the sensor 105 may be configured to send position information and/or orientation information at 120 data points per second, or at a frequency 120 Hz. Additionally, transmission delay and/or latency may be caused by interference in data collection and/or interference related to environmental factors. Delay may also build up over time, such that the examination data falls out of sync with the position information and/or orientation information. Thus, excessive delay, if unaccounted for, can render an examination data set unusable. In such cases, the computing system 500 may be configured to account for the delay and/or latency in data transmission from the NDE probe 100 and/or the sensor 105 to the computing system 500.

It should be noted that, occasionally the NDE probe 100 may deliver poor data points outside the range of possible values. In some instances, data points outside a range of possible values may occur when the NDE probe 100 changes its position and/or orientation, thereby causing the transducer 510 to become separated from the object 600. In various example embodiments, the computing system 500 in operation S850 may filter out these data points in order to reduce or otherwise prevent skewed results and/or inaccurate data visualizations. In such embodiments, in order to filter and deliver results without manual data manipulation, the computing system 500 may require input regarding basic inspection information, such as the expected range of the data of interest, the expected tracking area, and/or the rate of incoming information. In other example embodiments, the computing system 500 may provide a visual, aural, and/or tactile signal to the operator of the NDE probe 100 to warn the operator that the NDE probe 100 is producing poor data points outside the range of possible values.

As shown in operation S855, the computing system 500 determines whether the examination has been completed. If in operation S855 the computing system 500 determines that the examination is not complete, then the computing system 500 proceeds to operation S860 to instruct the NDE probe 100 to change a position and/or orientation of the NDE probe 100. If in operation S855 the computing system 500 determines that the examination is complete, then the computing system 500 proceeds to operation S870 to determine the characteristics of the object 600.

As shown in operation S860, the computing system 500 instructs the NDE probe 100 to change a position and/or orientation of the NDE probe 100. In various example embodiments, the NDE probe 100 may have the capability to move around an environment. In various example embodiments, the computing system 500 may instruct or otherwise control the NDE probe 100 to change its position based on a desired (or alternatively "predetermined") trajectory. Such a trajectory may be determined or otherwise defined by a human operator who determines where and how the NDE probe 100 is to reach various goals and or waypoints along the way. In some embodiments, the NDE probe 100 may include an autonomous position and/or orientation changing mechanism, which allows the NDE probe 100 to change its current position and/or orientation based on knowledge of its current position and/or orientation. Knowledge of the current position and/or orientation (i.e., "localization") may be calculated by one or more sensors such motor encoders, vision, stereopsis, lasers, and/or global positioning systems (GPS). Knowledge of the current position and/or orientation may also be fed to the NDE probe 100 by the computing system 500, which may determine the current position and/or orientation of the NDE probe 100.

Once the computing system 500 instructs the NDE probe 100 to change a position and/or orientation, the computing system 500 proceeds back to operation S820 to determine position information and/or orientation information of the NDE probe 100.

Referring back to operation S855, if in operation S855 the computing system 500 and/or the operator determines that the examination is complete, then the computing system 500 proceeds to operation S870 to determine characteristics of the object 600 including whether any indications of a deficiency exists in the object 600.

As shown in operation S870, the computing system 500 determines characteristics of the object 600 including whether any indications of a deficiency exists in the object 600. As discussed above, the received examination data is correlated with the position and/or orientation of the examination point by defining a relationship or otherwise associating the received examination data with the position information and/or orientation information. In operation S870, the computing system may produce a visual and/or data representation of the encoded examination data. The examination data may be processed based on the testing method used. For ultrasonic testing, the computing system 500 may produce, based on the signal received from the NDE probe 100, a waveform or other like visual representation that represents the signals emitted and the return or echo signals moving through object 600. Such a waveform may indicate depth information or other like characteristic information of the examined object. The depth information or other like characteristic information may be plotted against the position and/or orientation information of the examination point. In various example embodiments, a cloud of points, which may be colorized to represent depth data, may be used to create a heat map of thin areas and thick areas of the examination object.

As shown in operation S880, the examination data encoding routine 570 ends.

As will be appreciated, the technical effect of the methods, systems and apparatuses according the example embodiments allows for a computer-implemented system to efficiently and accurately perform a nondestructive examination of an object that may have a complex geometry and/or an object that covers a relatively large area, in addition to efficiently and accurately correlating examination data obtained during a nondestructive examination with position information and/or orientation information of a NDE probe that obtains the examination data.

As will be appreciated, the methods, systems and apparatuses according the example embodiments have several advantages. First, the example embodiments allow examinations to be performed without costly and/or customized machinery. Second, the example embodiments are cost-effective because the example embodiments provide a more accurate encoding of examinations on objects having a complex geometry and which cover large areas.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed:

1. A system for conducting Non-Destructive Examination (NDE) inspections and integrating inspection data with encoding information, comprising:
    a NDE probe configured to conduct a non-destructive examination of an object and output examination data;
    a shape sensing fiber optic cable attached to the NDE probe, the fiber optic cable configured to receive a frequency of light and to reflect the received light;
    a fiber optic cable shape sensing detector configured to generate light of the frequency, measure the shape of the shape sensing fiber optic cable based on the reflected light from the shape sensing fiber optic cable, and determine position information and orientation information of the NDE probe based on the measured shape of the fiber optic cable; and
    at least one processor configured to encode the examination data, the encoding including correlating the position information and the orientation information with the examination data,
        the determined position information including information regarding X-axis position, Y-axis position, and Z-axis position of the NDE probe,
        the determined orientation information including information regarding yaw angle, pitch angle, and roll angle of the NDE probe,
    the encoded examination data used to determine whether there is an indication within the object.

2. The system of claim 1, wherein
the fiber optic cable is configured to receive varying frequencies of light; and
the fiber optic cable shape sensing detector is configured to generate the varying frequencies of light.

3. The system of claim 1, wherein the shape sensing fiber optic cable includes at least one fiber optic core.

4. The system of claim 1, wherein the shape sensing fiber optic cable includes a plurality of fiber optic cores woven together in a helical manner.

5. The system of claim 1, wherein the shape sensing fiber optic cable includes a plurality of fiber optic cores configured in a geometric shape.

6. The system of claim 1, wherein the NDE probe includes an ultrasonic transducer/receiver.

7. The system of claim 1, wherein the at least one processor is further configured to:

determine whether the encoded examination data is outside of an expected data range; and generate a visual, aural, or tactile signal to an operator of the NDE probe based on results of the determination of whether the encoded examination data is outside of the expected data range.

8. The system of claim 1, wherein the at least one processor is configured to encode the examination data in real-time.

9. The system of claim 1, wherein the NDE probe is coupled to a robot configured to traverse the object.

10. The system of claim 1, wherein the at least one processor is configured to produce a 3D representation of the object based on the encoded information and transmit the 3D representation of the object to a display.

11. The system of claim 1, wherein the shape sensing fiber optic cable includes Bragg gratings.

12. The system of claim 1, wherein the fiber optic cable shape sensing detector is configured to measure the shape of the shape sensing fiber optic cable by comparing the frequency of the reflected light with the frequency of the generated light.

13. The system of claim 1, wherein the fiber optic cable shape sensing detector is configured to measure the shape of the shape sensing fiber optic cable by comparing a Rayleigh back scatter pattern of the shape sensing fiber optic cable with a reference Rayleigh back scatter pattern.

14. The system of claim 1, wherein the NDE probe performs at least one of an acoustic emission testing (AE), an electromagnetic testing (ET), a laser testing methods (LM), a leak testing (LT), a magnetic flux leakage (MFL), a liquid penetrant testing (PT), a magnetic particle testing (MT), a neutron radiographic testing (NR), a radiographic testing (RT), a thermal/infrared testing (IR), an ultrasonic testing (UT), a vibration analysis (VA), a visual testing (VT), a remote visual inspection (RVI), an eddy-current testing (ECT), and a low coherence interferometry (LCI).

15. A method for conducting Non-Destructive Examination (NDE) inspections and integrating inspection data with encoding information, comprising:
   conducting a non-destructive examination of an object using a NDE probe and outputting examination data;
   determining a shape of a shape sensing fiber optic cable attached to the NDE probe, the determining including,
      generating, by a fiber optic cable shape sensing detector, a frequency of light,
      reflecting, by the shape sensing fiber optic cable, the frequency of light,
      measuring, by the fiber optic cable shape sensing detector, the shape of the shape sensing fiber optic cable based on the reflected light from the shape sensing fiber optic cable, and
   determining position information and orientation information of the NDE probe based on the measured shape of the fiber optic cable,
      the determining position information including determining X-axis position, Y-axis position, and Z-axis position of the NDE probe, and
      the determining orientation information including determining yaw angle, pitch angle, and roll angle of the NDE probe;
   encoding the examination data, the encoding including correlating the position information and the orientation information with the examination data; and
   determining whether there is an indication within the object based on the encoded examination data.

16. The method of claim 15, wherein
   the generating the frequency of light includes generating varying frequencies of light; and
   the reflecting the frequency of light includes reflecting the varying frequencies of light.

17. The method of claim 15, wherein the determining the shape of the shape sensing fiber optic cable includes determining a shape of at least one fiber optic core.

18. The method of claim 15, wherein the determining the shape of the shape sensing fiber optic cable includes determining shapes of a plurality of fiber optic cores woven together in a helical manner.

19. The method of claim 15, wherein the determining the shape of the shape sensing fiber optic cable includes determining shapes of a plurality of fiber optic cores configured in a geometric shape.

20. The method of claim 15, wherein the conducting the non-destructive examination of the object includes conducting an ultrasonic examination of the object.

21. The method of claim 15, further comprising:
   determining whether the encoded examination data is outside of an expected data range; and
   generating a visual, aural, or tactile signal to an operator of the NDE probe based on results of the determination of whether the encoded examination data is outside of the expected data range.

22. The method of claim 15, wherein the encoding is conducted in real-time.

23. The method of claim 15, wherein the conducting is performed by a robot coupled to the NDE probe, the robot configured to traverse the object.

24. The method of claim 15, further comprising:
   producing a 3D representation of the object based on the encoded information; and
   transmitting the 3D representation of the object to a display.

25. The method of claim 15, wherein the measuring the shape of the shape sensing fiber optic cable includes comparing the frequency of the reflected light with the frequency of the generated light.

26. The method of claim 15, wherein the measuring the shape of the shape sensing fiber optic cable includes measuring the frequency of light reflected off of at least one Bragg grating within the shape sensing fiber optic cable.

27. The method of claim 15, wherein the measuring the shape of the shape sensing fiber optic cable includes measuring a Rayleigh back scatter pattern of the shape sensing fiber optic cable and comparing the measured Rayleigh back scatter pattern with a reference Rayleigh back scatter pattern of the shape sensing fiber optic cable.

28. The method of claim 15, wherein the conducting includes performing at least one of: an emission testing (AE), an electromagnetic testing (ET), a laser testing methods (LM), a leak testing (LT), a magnetic flux leakage (MFL), a liquid penetrant testing (PT), a magnetic particle testing (MT), a neutron radiographic testing (NR), a radiographic testing (RT), a thermal/infrared testing (IR), an ultrasonic testing (UT), a vibration analysis (VA), a visual testing (VT), a remote visual inspection (RVI), an eddy-current testing (ECT), and a low coherence interferometry (LCI).

* * * * *